United States Patent
Vogt et al.

(10) Patent No.: US 9,956,019 B2
(45) Date of Patent: May 1, 2018

(54) DISPENSING DEVICE WITH ELASTICALLY DRIVEN MIXER

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 195 days.

(21) Appl. No.: 14/829,836

(22) Filed: Aug. 19, 2015

(65) Prior Publication Data

US 2016/0051305 A1 Feb. 25, 2016

(30) Foreign Application Priority Data

Aug. 22, 2014 (DE) .......................... 10 2014 112 042

(51) Int. Cl.
*A61B 17/00* (2006.01)
*B01F 7/00* (2006.01)
(Continued)

(52) U.S. Cl.
CPC ...... *A61B 17/8833* (2013.01); *B01F 7/00183* (2013.01); *B01F 11/0054* (2013.01);
(Continued)

(58) Field of Classification Search
CPC ......... A61B 17/8833; A61B 2017/8838; B01F 7/00183; B01F 11/0054; B01F 13/003;
(Continued)

(56) References Cited

U.S. PATENT DOCUMENTS

| 4,671,263 A | 6/1987 | Draenert |
| 4,758,096 A | 7/1988 | Gunnarsson |

(Continued)

FOREIGN PATENT DOCUMENTS

| CN | 202 87 5453 U | 4/2013 |
| DE | 36 40 279 A1 | 6/1987 |

(Continued)

OTHER PUBLICATIONS

Canadian Office Action for corresponding Canadian Application No. 2,899,554 dated Jul. 27, 2016.
(Continued)

*Primary Examiner* — Anshu Bhatia
(74) *Attorney, Agent, or Firm* — Norris McLaughlin & Marcus P.A.

(57) ABSTRACT

A mixing device comprises a mixing space for mixing bone cement, at least one mixing element supported in the mixing space such that it can rotate, a gear for rotating the at least one mixing element, and at least one elastically deformable energy-storing element that is connected to the gear such that the gear can be driven by an elastic energy from the energy-storing element and such that the at least one mixing element can be rotated in the mixing space by means of the gear upon the release of elastic energy from the energy-storing element. Additionally, a vacuum mixing system and mixing method comprise the mixing device for mixing the bone cement.

16 Claims, 5 Drawing Sheets

Figure 1:
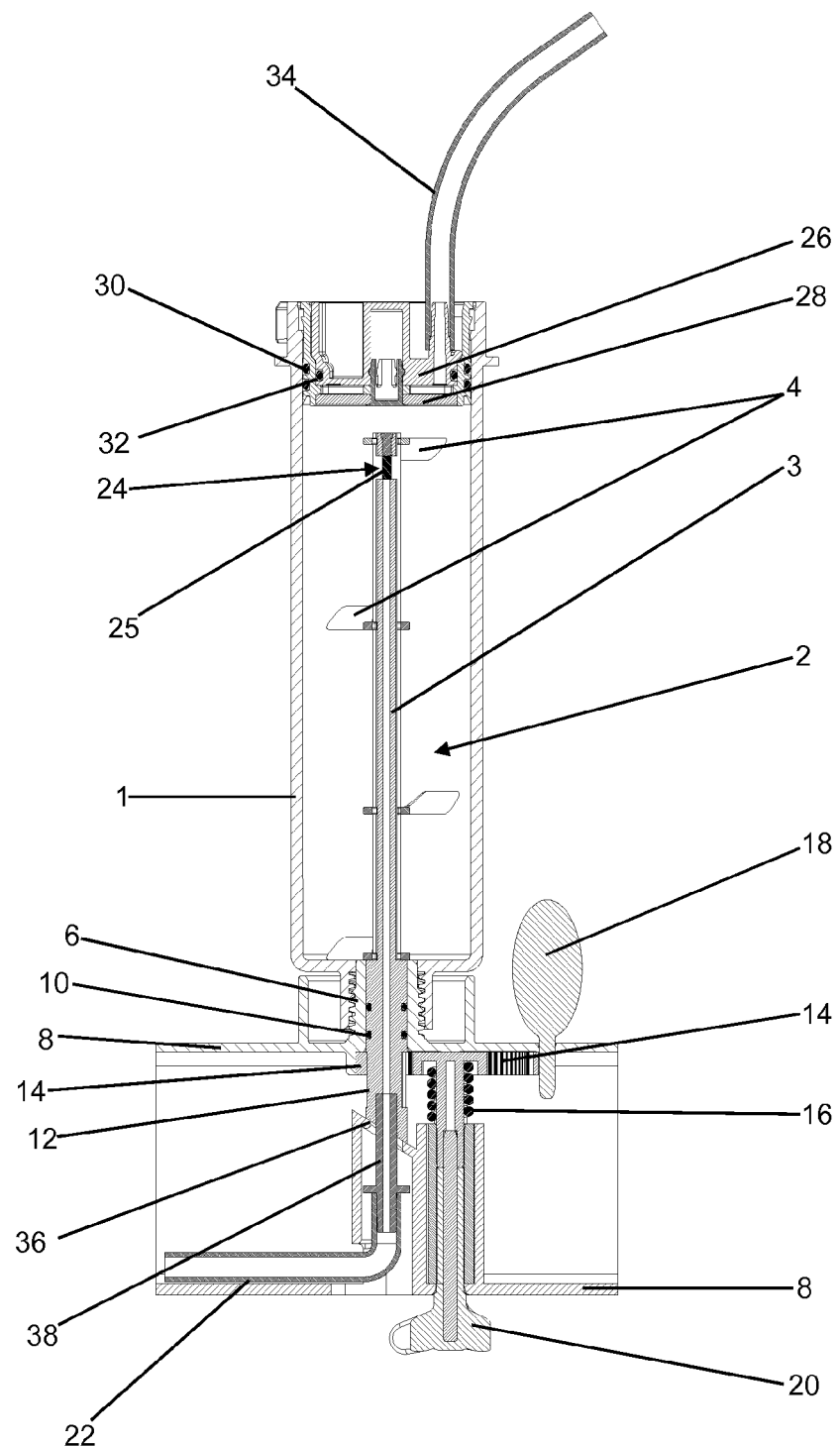

(51) Int. Cl.
- *B01F 13/00* (2006.01)
- *A61B 17/88* (2006.01)
- *B01F 11/00* (2006.01)
- *B01F 15/00* (2006.01)
- *B01F 15/02* (2006.01)
- *F03G 1/02* (2006.01)

(52) U.S. Cl.
CPC ...... *B01F 13/003* (2013.01); *B01F 15/00487* (2013.01); *B01F 15/0258* (2013.01); *B01F 15/0279* (2013.01); *F03G 1/02* (2013.01); *A61B 2017/8838* (2013.01); *B01F 2215/0029* (2013.01)

(58) Field of Classification Search
CPC ............ B01F 15/00487; B01F 15/0258; B01F 15/0279; B01F 2215/0029; F03G 1/02
See application file for complete search history.

(56) References Cited

U.S. PATENT DOCUMENTS

| | | | |
|---|---|---|---|
| 4,832,501 A * | 5/1989 | McCauley | ............ B01F 7/0015 366/279 |
| 4,973,168 A | 11/1990 | Chan | |
| 5,100,241 A | 3/1992 | Chan | |
| 5,201,263 A | 4/1993 | Teng | |
| 5,344,232 A | 9/1994 | Nelson et al. | |
| 5,348,391 A | 9/1994 | Murray | |
| 5,497,695 A | 3/1996 | Canela | |
| 5,551,778 A | 9/1996 | Hauke et al. | |
| 5,586,821 A | 12/1996 | Bonitati et al. | |
| 5,588,745 A | 12/1996 | Tanaka et al. | |
| 5,624,184 A | 4/1997 | Chan | |
| 5,997,544 A | 12/1999 | Nies et al. | |
| 6,033,105 A | 3/2000 | Barker et al. | |
| 6,709,149 B1 | 3/2004 | Tepic | |
| 7,073,936 B1 | 7/2006 | Jonsson | |
| 2008/0144428 A1 | 6/2008 | Berelsman et al. | |
| 2010/0329074 A1 | 12/2010 | Vogt et al. | |
| 2013/0135957 A1 | 5/2013 | Vogt et al. | |
| 2013/0135959 A1 | 5/2013 | Vogt et al. | |

FOREIGN PATENT DOCUMENTS

| | | |
|---|---|---|
| DE | 197 45 084 C2 | 6/2001 |
| DE | 698 12 726 T2 | 2/2004 |
| DE | 10 2009 031 178 B3 | 9/2010 |
| DE | 10 2011 119 371 B3 | 4/2013 |
| DE | 10 2011 119 377 B3 | 4/2013 |
| EP | 0 692 229 A1 | 1/1996 |
| EP | 1 005 901 A2 | 6/2000 |
| EP | 1 016 452 A2 | 7/2000 |
| EP | 1 020 167 A2 | 7/2000 |
| WO | 94/26403 A1 | 11/1994 |
| WO | 98/39088 A1 | 9/1998 |
| WO | 99/67015 A1 | 12/1999 |

OTHER PUBLICATIONS

Japanese Office Action for corresponding Japanese Application No. 2015-164271 dated Oct. 4, 2016.
Australian Examination Report from corresponding Australian Application No. 2015207434 dated Jun. 15, 2016.
European Search Report dated Jan. 18, 2016.
German Office Action dated Apr. 24, 2015.
Australian Examination Report dated Jan. 8, 2016.

* cited by examiner

DISPENSING DEVICE WITH ELASTICALLY DRIVEN MIXER

The invention relates to a mixing device for polymethylmethacrylate bone cements (PMMA bone cements).

The invention further relates to a vacuum mixing system comprising a mixing device of this type and to a method for mixing a cement, in particular a PMMA bone cement.

Accordingly, the subject matter of the invention is a mixing device for homogenisation of cement components of powder-liquid polymethylmethacrylate bone cements. Another subject matter of the invention is a closed vacuum mixing system for the storage, mixing, and dispensing of polymethylmethacrylate bone cement.

Polymethylmethacrylate (PMMA) bone cements are based on the pioneering work of Sir Charnley. PMMA bone cements consist of a liquid monomer component and a powder component. The monomer component generally contains the monomer, methylmethacrylate, and an activator (N,N-dimethyl-p-toluidine) dissolved therein. The powder component, which is also referred to as bone cement powder, comprises one or more polymers, a radiopaquer, and the initiator dibenzoylperoxide. The polymers of the powder component are produced on the basis of methylmethacrylate and comonomers, such as styrene, methylacrylate or similar monomers by means of polymerisation, preferably by suspension polymerisation. During the mixing of powder component and monomer component, swelling of the polymers of the powder component in the methylmethacrylate generates a dough that can be shaped plastically and is the actual bone cement. During the mixing of powder component and monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

PMMA bone cements can be mixed by mixing the cement powder and the monomer liquid in suitable mixing beakers with the aid of spatulas. One disadvantage of said procedure is that air inclusions may be present in the cement dough thus formed and can cause destabilisation of the bone cement later on. For this reason, it is preferred to mix bone cement powder and monomer liquid in vacuum mixing systems, since mixing in a vacuum removes air inclusions from the cement dough to a large extent and thus achieves optimal cement quality. Bone cements mixed in a vacuum have clearly reduced porosity and thus show improved mechanical properties. A large number of vacuum cementing systems have been disclosed of which the following shall be listed for exemplary purposes: U.S. Pat. No. 6,033, 105 A, U.S. Pat. No. 5,624,184 A, U.S. Pat. No. 4,671,263 A, U.S. Pat. No. 4,973,168 A, U.S. Pat. No. 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, U.S. Pat. No. 5,344,232 A.

Cementing systems, in which both the cement powder and the monomer liquid are already packed in separate compartments of the mixing systems and are mixed with each other in the cementing system only right before application of the cement, are a development of cementing technology. Said full-prepacked mixing systems were proposed through EP 0 692 229 A1, DE 10 2009 031 178 B3, U.S. Pat. No. 5,997,544 A, U.S. Pat. No. 6,709,149 B1, DE 698 12 726 T2, and U.S. Pat. No. 5,588,745 A.

Patent DE 10 2009 031 178 B3 discloses a closed vacuum mixing system having a two-part dispensing plunger for closure of a cement cartridge. A combination of a gas-permeable sterilisation plunger and a gas-impermeable sealing plunger is used in this context. The starting components are mixed in the mixing space by moving mixing vanes that are attached to a mixing rod. Said motion is effected by manually pushing, pulling, and rotating the mixing run in and out, whereby the mixing rod is guided out from the mixing space through a bushing and terminates in a handle that can be operated by hand. This principle of a closed vacuum mixing system is implemented in the closed cementing system, PALACOS® PRO, made and distributed by Heraeus Medical GmbH.

In the vacuum mixing systems that were conventional until now, the mixing is effected by mixing devices that can be operated by hand. The mixing results are reproducible only to a degree, which is due to individual influences of the users, such as different energy input due to variable mixing intensity and mixing time. This means that the cement properties may show variation. Moreover, mixing the PMMA bone cement always requires some work effort, which may be an impediment in the often hectic routine during surgeries. Insufficient mixing of the bone cement can lead to a deterioration of the connection of the cemented bones and prostheses, which is absolutely undesired.

Accordingly, it is the object of the invention to overcome the disadvantages of the prior art. Specifically, a mixing device for polymethylmethacrylate bone cement is to provided, in which the process of mixing the cement powder with the monomer liquid can proceed reproducibly and independent of the medical user. The mixing device shall work independent of external energy sources. Moreover, a closed vacuum mixing system that has the mixing device integrated into it is to be developed. The vacuum mixing system is to contain a cement cartridge, in which the cement powder is stored, as well as a separate reservoir container, in which the monomer liquid is situated. Accordingly, the monomer liquid is stored separate from the cement powder. Any contact of the medical users with said components shall be excluded before and after the mixing of the two cement components, i.e. the cement powder and the monomer liquid. Therefore, the reservoir container shall be opened and the monomer shall be transferred in a closed system. The cement powder must not contact the medical user either. In addition, the device shall be as easy as possible to use and still yield a well-mixed bone cement dough.

The objects of the invention are met by a mixing device for polymethylmethacrylate bone cements (PMMA bone cements), comprising a mixing space for mixing the PMMA bone cement;

at least one mixing element supported in the mixing space such that it can rotate; a gear, by means of which the rotation of the at least one mixing element can be driven;

at least one elastically deformable energy-storing element that is connected to the gear such that the gear can be driven by an elastic energy from the energy-storing element and such that the at least one mixing element can be rotated in the mixing space by means of the gear upon the release of elastic energy from the energy-storing element.

According to the invention, it is sufficient if the elastically deformable energy-storing element contains the energy for a single mixing process of the starting components of the PMMA bone cement by means of the at least one mixing element.

The PMMA bone cement is preferably mixed from two components, whereby the first component is a powder or a paste and the second component is fluid, preferably is liquid, particularly preferably a cement powder and a monomer liquid.

Mixing devices according to the invention can provide the at least one mixing element to be arranged on a stirrer shaft that is supported such that it can rotate, and can provide the gear to drive a rotation of the stirring shaft, whereby the stirrer shaft preferably is guided through a gas-tight or pressure-tight bushing out of the mixing space and is connected to the gear outside the mixing space.

The stirrer shaft is particularly well-suited for transferring energy from the elastically deformable energy-storing element, since it allows a rotary motion to be transferred particularly efficiently. Moreover, a stirrer shaft of this type can be supported particularly well and can be sealed at the passage into the mixing space.

The invention can provide the gear to be connected to the stirrer shaft in a form-fitting or force-blocking manner. This enables a stable and robust drive with low energy losses.

Mixing devices having a stirrer shaft can also be provided such that the stirrer shaft is hollow and forms a conduit for a liquid starting component of the PMMA bone cement, preferably a conduit for a monomer liquid as starting component of the PMMA bone cement. In this context, the stirrer shaft is hollow on the inside.

As a result, the liquid starting component can be guided into the inside of the mixing space. Specifically, during a periodic linear axial motion of the stirrer shaft, a better distribution of the liquid and/or fluid starting component, in particular of the monomer liquid, in the other starting component, in particular in the cement powder, in the mixing space can be attained.

A refinement of the present invention proposes the at least one mixing element to be a plurality of mixing vanes, whereby the mixing vanes extend into the mixing space such as to be radial to the rotation axis during the rotation of the mixing vanes in the mixing space and are inclined with respect to a plane perpendicular to the rotation axis.

Mixing vanes are particularly well-suited for mixing in the internal space, since they can be used with little effort and attain a good mixing effect with little resistance while cutting through the PMMA bone cement dough.

In this context, the invention can provide the mixing vanes to be attached or attachable to the stirrer shaft, whereby the mixing vanes are arranged on the stirrer shaft at an axial offset from each other.

As a result, good mixing of the PMMA bone cement over the entire axial length of the mixing space is attained.

In turn, the invention can provide the mixing vanes to be attached to the stirrer shaft by means of a joint, such that the mixing vanes can be placed against the stirrer shaft.

As a result, the stirrer shaft with attached mixing vanes is easier to insert and/or retract into and from the mixing space.

Mixing devices with mixing vanes can also be provided appropriately such that the mixing vanes are attached to the stirrer shaft in detachable manner, such that the mixing vanes can be separated, in particular broken off, from the stirrer shaft while the stirrer shaft is being pulled out of the mixing space.

In this case, the mixing vanes remain the mixing space. As a result, the stirrer shaft can be comfortably removed from and/or pulled out of the mixing space without the mixing vanes preventing or impeding this process. Specifically, the stirrer shaft can also be pulled out of the bushing for the stirrer shaft into the mixing space.

A refinement of the mixing device according to the invention can provide the gear and/or the elastically deformable energy-storing element to be locked by means of at least one detachable mechanical lock such that a release of the energy from the energy-storing element is prevented, whereby the at least one mechanical lock is preferred to be a safety catch and/or a safety pin.

As a result, the triggering and application of the mixing device can become particularly easy and user-friendly. The mechanical lock prevents an inadvertent release of the elastic energy from the elastic energy-storing element. Once the mechanical lock is detached, the elastic energy is released from the energy-storing element.

According to a preferred embodiment, the invention can provide the gear to be a cogwheel gear or a friction wheel gear or a power transmission gear.

Due to their simple and inexpensive design and insensitivity to errors, said gears are particularly well-suited for designing mixing devices according to the invention.

Moreover, the invention can provide the elastically deformable energy-storing element to be a spring element that is connected to the gear, whereby the gear can be driven by the spring force of the tensioned spring element, whereby the spring element is preferred to be a spring element that is or can be tensioned, particularly preferably a metal spring, even more preferably a steel leg spring, a steel leaf spring or a steel coil spring.

Said spring elements allow a particularly easy and inexpensive design to be implemented, since they are particularly well-suited for driving rotary motions. In the scope of the present invention, it was found that the amount of elastic energy stored in a spring element of this type, provided it is dimensioned to match the size of the mixing device and/or to match the size of a vacuum mixing system including it, is suitable for sufficient mixing even of viscous PMMA bone cements.

The invention can further provide that a release of elastic energy from the energy-storing element effects a rotary motion of the gear, that the gear effects a transmission ratio of at least 2:1 with respect to the at least one mixing element, preferably a transmission ratio of at least 5:1, particularly preferably of at least 8:1, with respect to the at least one mixing element.

In this context, a transmission ratio of at least 2:1 means that one rotation of the gear is associated with at least two rotations of the at least one mixing element in the mixing space. Preferably, the gear effects a transmission racial of maximally 32:1, particularly preferably of maximally 20:1, to the at least one mixing element. Said transmission ratio effects strong mixing of the PMMA bone cement and produces the high torque required for mixing of the viscous PMMA bone cement dough.

A refinement of the invention proposes that the motion of the at least one mixing element during the rotary motion can be influenced by means of a cam disc such that the at least one mixing element also performs a periodical axial stroke motion during the rotary motion, whereby it is preferred that the axial motion of the stirrer shaft can be generated by the cam disc such that the stirrer shaft also performs a periodical axial stroke motion during the rotary motion.

As a result, the mixing effect is improved by the axial motion of the mixing element in the mixing space.

The objects underlying the present invention are also met by a vacuum mixing system for mixing a PMMA bone cement, comprising a mixing device according to the invention, further comprising the mixing space that contains a cement powder;
a monomer container that is filled with a fluid or liquid monomer; and a conduit means that connects the monomer container to the mixing space in liquid-permeable manner or by means of which the monomer container can be connected to the mixing space in liquid-permeable manner.

This results in a complete device being generated by means of which a PMMA bone cement and its starting components can be stored and mixed.

Vacuum mixing systems of this type can be provided appropriately such that the vacuum mixing system comprises a base at which the mixing space is attached in detachable manner and at which the monomer container is attached, whereby the conduit means and the elastic energy-storing element are arranged in or on the base.

As a result, the design and the application of the vacuum mixing system are simplified and stabilised.

Moreover, the invention can provide a drive axle, in particular the stirrer shaft, to extend through a seal out of the mixing space and a cogwheel or friction wheel to be attached on the part of the drive axle, in particular of the stirrer shaft, that is arranged outside of the mixing space and to be connected to the gear, preferably to a cogwheel, friction wheel, toothed belt or friction belt of the gear, whereby the drive axle, in particular the stirrer shaft, can be driven by means of the cogwheel or friction wheel.

As a result, a vacuum mixing system with a particularly simple and inexpensive design that works reliably and insensitive to errors can be attained.

Moreover the invention can provide the mixing space to be a part of a cement cartridge, whereby the cement cartridge is closed on one side by a dispensing plunger or a dispensing plunger system, whereby the dispensing plunger or the dispensing plunger system is axially mobile in the mixing space and is intended for expelling the ready-mixed PMMA bone cement, and can provide the closure thus formed to be impermeable for the cement powder particles and to be permeable for gas, in particular for ethylene oxide, whereby the cement cartridge, before the cement components are being mixed, can be closed appropriately in vacuum-tight manner such that a transfer of the monomer liquid into the mixing space of the cement cartridge to the cement powder under the effect of a vacuum is made feasible.

As a result, the vacuum mixing system is also well-suited for sterilisation and dispensing of the ready-mixed PMMA bone cement as well as for mixing in a vacuum.

The invention can just as well provide a device for generating a vacuum to be integrated into the vacuum mixing system.

As a result, the vacuum mixing system is made even more comprehensive and independent of an external vacuum source.

The objects underlying the present invention are also met by a method for the mixing of a cement, in particular of a PMMA bone cement, in which at least two starting components of the cement are mixed in a mixing space by at least one mixing element, whereby the at least one mixing element is rotated in the mixing space about a rotation axis and, in the process, mixes the starting components in the mixing space, whereby the rotation of the at least one mixing element is driven by means of a gear and the energy driving the gear is removed from an elastically deformed energy-storing element, whereby the elastically deformed energy-storing element relaxes while the energy is being removed.

Preferably, the invention can provide the mixing space to be closed while the starting components are being mixed, preferably to be closed in gas-tight and/or pressure-tight manner, in this context.

The method according to the invention further proposes to perform the method by means of a mixing device according to the invention or of a vacuum mixing system according to the invention.

Moreover, the invention can provide a first starting component to be powdery and to already be present in the mixing space, and a second starting component to be a liquid that is guided into the mixing space, preferably that is aspirated into the mixing space by means of a vacuum.

A refinement proposes to periodically move the mixing element in axial direction and, in the process, to mix the starting components in the mixing space.

Moreover, the invention can provide the periodical axial motion of the at least one mixing element to be driven by means of a cam disc and a gear, and the energy for driving the gear and the motion of the cam disc to be removed from the elastically deformed energy-storing element, whereby the elastically deformed energy-storing element relaxes while the energy is being removed.

The invention can provide just as well for a stirrer shaft to which the at least one mixing element, in the form of mixing vanes, is attached to be pulled out of the mixing space after the cement is mixed, whereby the mixing vanes break off and remain in the mixing space or the mixing vanes become placed against the stirrer shaft and are pulled out of the mixing space together with the stirrer shaft.

Preferably, the invention can just as well provide the energy-storing element to be a tensioned metal spring that relaxes upon the release of elastic energy to the gear and thus drives the gear.

Preferably, a tensioned coil spring made of steel as the energy-storing element unwinds for the release of elastic energy to the gear.

And lastly the invention can provide the elastic energy to be removed from the energy-storing element by detaching a mechanical lock that locks the gear and/or the elastically deformable energy-storing element, whereby, after said detachment, the elastic energy is released from the energy-storing element to the gear, whereby it is preferred to use a safety catch and/or a safety pin as mechanical lock, which particularly preferably engages the gear and arrests the gear.

The invention is based on the surprising finding that the relaxation of an elastically deformed energy-storing element that drives the mixing element by means of a gear allows a mixing device and a vacuum mixing system for PMMA bone cements as well as a method for the mixing of a cement, in particular of a PMMA bone cement, to be provided, in which no manual mixing of the PMMA bone cement is required and in which the energy for the mixing of the PMMA bone cement is already stored. As a result, an external energy source is made superfluous. In this context, the devices according to the invention and the method according to the invention work exclusively in the absence of electrical drives or motors and are well-suited even for viscous PMMA bone cements. The standardisation of the mixing process allows irregularities and differences in the physical properties of the ready-mixed PMMA bone cements to be reduced or even excluded. The application is simplified markedly, which has a beneficial effect especially in the often hectic routines during a surgery. In this context, the design remains inexpensive and the product can therefore also be offered as a disposable article, which makes sense considering the hygienic requirements in the surgical area. Methods and devices according to the invention can be used to produce a PMMA bone cement of consistent quality. Moreover, the vacuum mixing system according to the invention is well-suited for storage of the starting components and for application of the ready-mixed bone cement.

Mixing devices according to the invention for PMMA bone cements can, for example comprise:
a) at least one stirrer shaft that is supported such that it can rotate and is connected to at least one mixing element;
b) a gear that is connected to the stirrer shaft in a form-fitting or force-locking manner;
c) at least one elastically deformable energy-storing element that is connected to the gear;
whereby the relaxation of the energy-storing element effects the rotary motion of the gear by means of which the gear transmits the rotary motion to the stirrer shaft that has the mixing element connected to it.

Metal springs are preferred as elastically deformable energy-storing element, whereby steel legs springs, steel leaf springs, and steel coil springs are particularly preferred. However, rods, coil springs made of elastomers can be used just as well.

The springs can be tensioned by deformation. This stores mechanical energy. The energy-storing element in the tensioned state is locked appropriately by at least one detachable mechanical lock of the gear such that a spontaneous inadvertent release of the energy of the energy-storing element is prevented, whereby said lock is preferably provided as a safety catch and/or as a safety pin. The lock can be detached directly from outside by the user. According to a variant that is particularly preferred according to the invention, the lock can be coupled to the triggering of other functions, such as, for example, the monomer container being opened.

The transmission of energy from the energy-storing element to the stirrer shaft and/or to the at least one mixing element requires that a gear is arranged in between these in order to be able to transfer a sufficient number of rotary motions to the stirrer shaft. In this context, a cogwheel gear or a friction wheel gear or a force transmission gear is preferred that generates, by transmission, at least two rotary motions, preferably at least five and particularly preferably at least eight revolutions of the stirrer shaft and/or of the at least one mixing element during the motion of the gear caused by the relaxation of the energy-storing element. In the force transmission gear, toothed belts and/or friction belts can be used for transfer of the torques and/or rotary motion. Alternatively, a cuter using toothed racks can be used just as well.

It is advantageous to have the stirrer shaft interact with at least one cam disc during the rotary motion, whereby the stirrer shaft performs a periodical axial stroke motion during the rotary motion. As a result, the at least one mixing element is moved up and down in the cartridge during its rotation. As a result, all regions on the inside of the mixing space are reached during the stirring motion provided the stirrer length and the cam disc are dimensioned appropriately. Consequently, there are no on non-mixed regions of cement powder and monomer liquid in the mixing space that are not being reached by the mixing element. It is advantageous in this context that the mixing element contains wiper elements that press elastically against the internal wall of the mixing space of the cement cartridge.

Another preferred embodiment is a vacuum mixing system with a mixing device according to the invention, comprising a mixing space, in which the cement powder is stored, a separate monomer container, a conduit means that connects the monomer container to the mixing space in liquid-permeable manner, and a foot part that is connected to the mixing space and the monomer container. The vacuum mixing system comprises, for example,
a) at least one rotatable stirrer shaft, whereby a first section of the stirrer shaft is arranged in the mixing space, which is connected to at least one mixing element, and a second section of the stirrer shaft is arranged outside the mixing space in a separate foot part, whereby said section is provided as a cogwheel or friction wheel at its end and is supported such that it can rotate about its longitudinal axis;
b) a cogwheel gear or friction wheel gear or force transmission gear that engages the end of the stirrer shaft that is provided as cogwheel or friction wheel, and
c) at least one spring that acts on the cogwheel gear or friction wheel gear or force transmission gear.

The vacuum mixing system according to the invention can also be characterised in that the at least one mixing element is reversibly connected to the stirrer shaft and in that it can be detached by being wiped off the stirrer shaft when the stirrer shaft is being pulled out.

In another variant of the vacuum mixing system, the at least one mixing element can be folded against the stirrer shaft when the stirrer shaft is pulled out of the mixing space. As a result, it is feasible to remove the stirrer shaft from the mixing space once the mixing of the cement components is completed.

Moreover, the vacuum mixing system according to the invention can be characterised in that the cement cartridge is closed by a plunger or plunger system that is impermeable for the particles of the cement powder, but is permeable for ethylene oxide during the sterilisation, and can be closed appropriately to be vacuum-tight before the mixing of the cement components such that the monomer liquid can be transferred into the mixing cartridge to the cement powder by the effect of a vacuum.

It is particularly advantageous to have a device for generating a vacuum integrated into the vacuum mixing system. Said device for generating a vacuum can, for example, itself be driven by a spring or a spring system. Besides, it is also feasible to generate the vacuum by means of an integrated compressed gas cartridge, whereby a Venturi nozzle is used to generate negative pressure.

Figure 2:
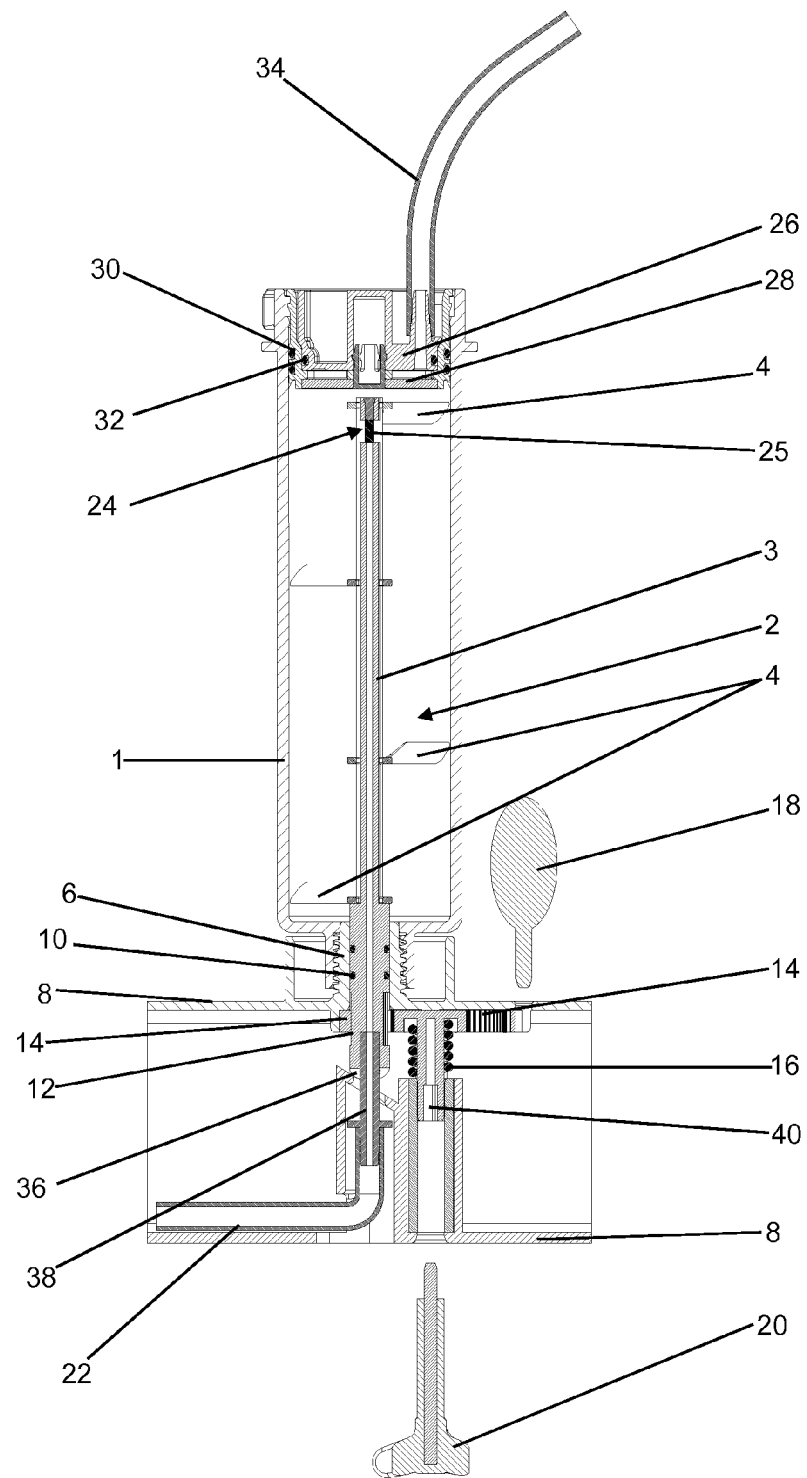
Figure 3:
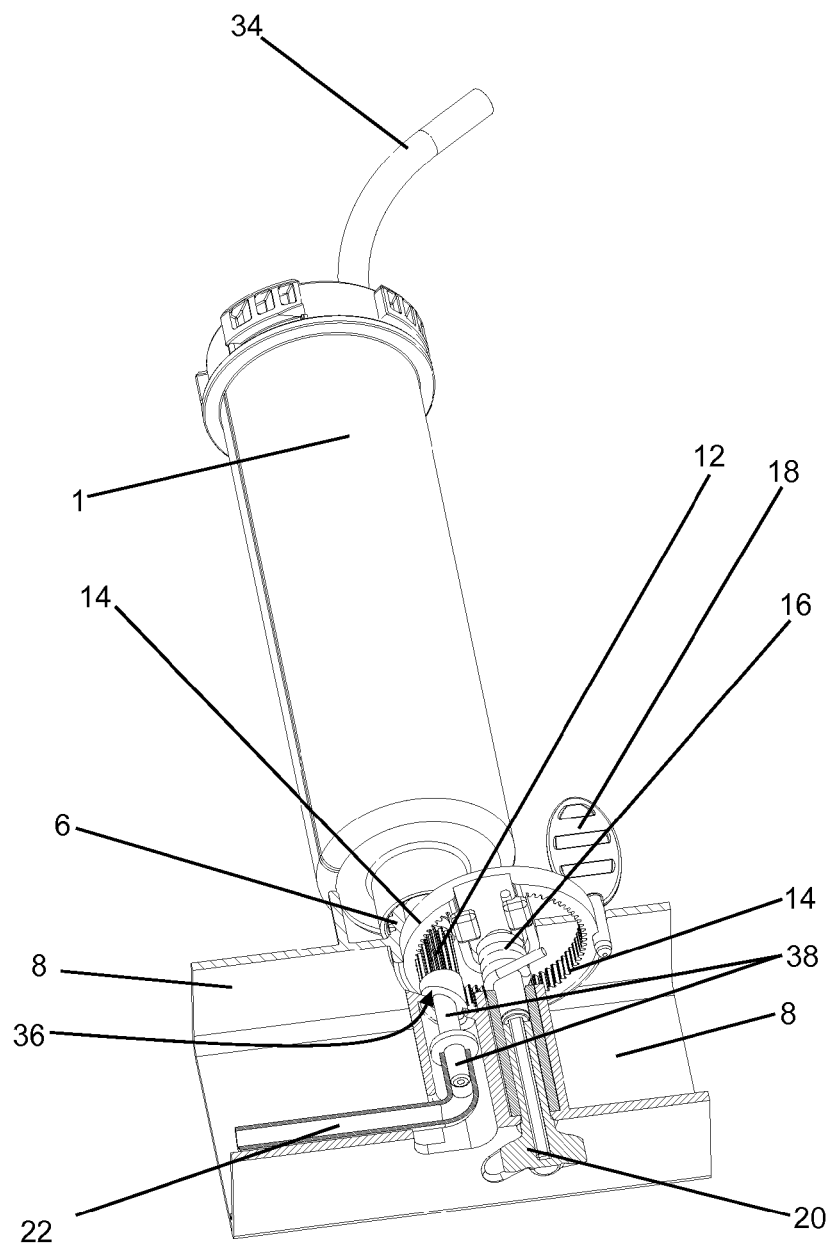
Figure 4:
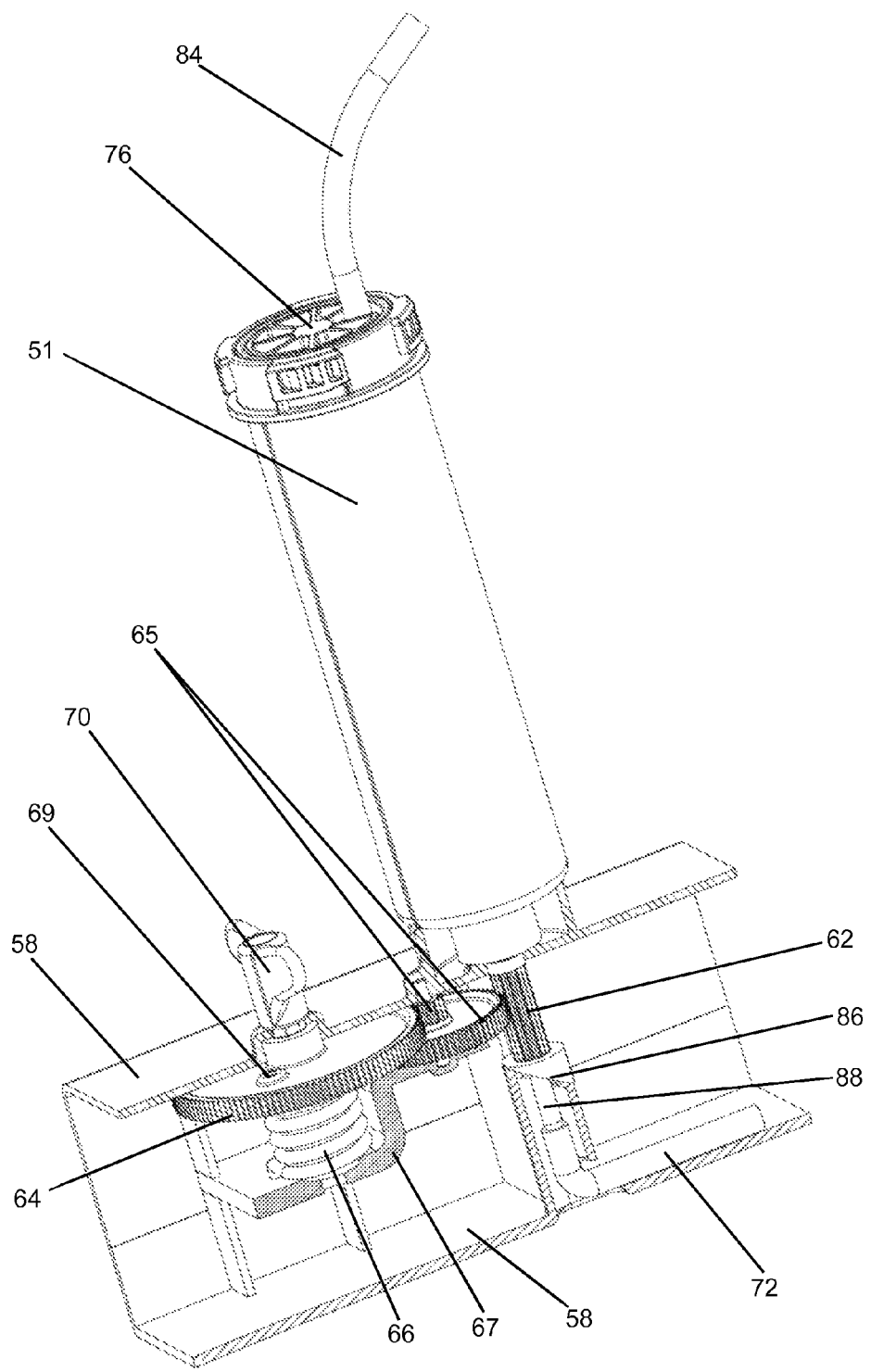
Figure 5:
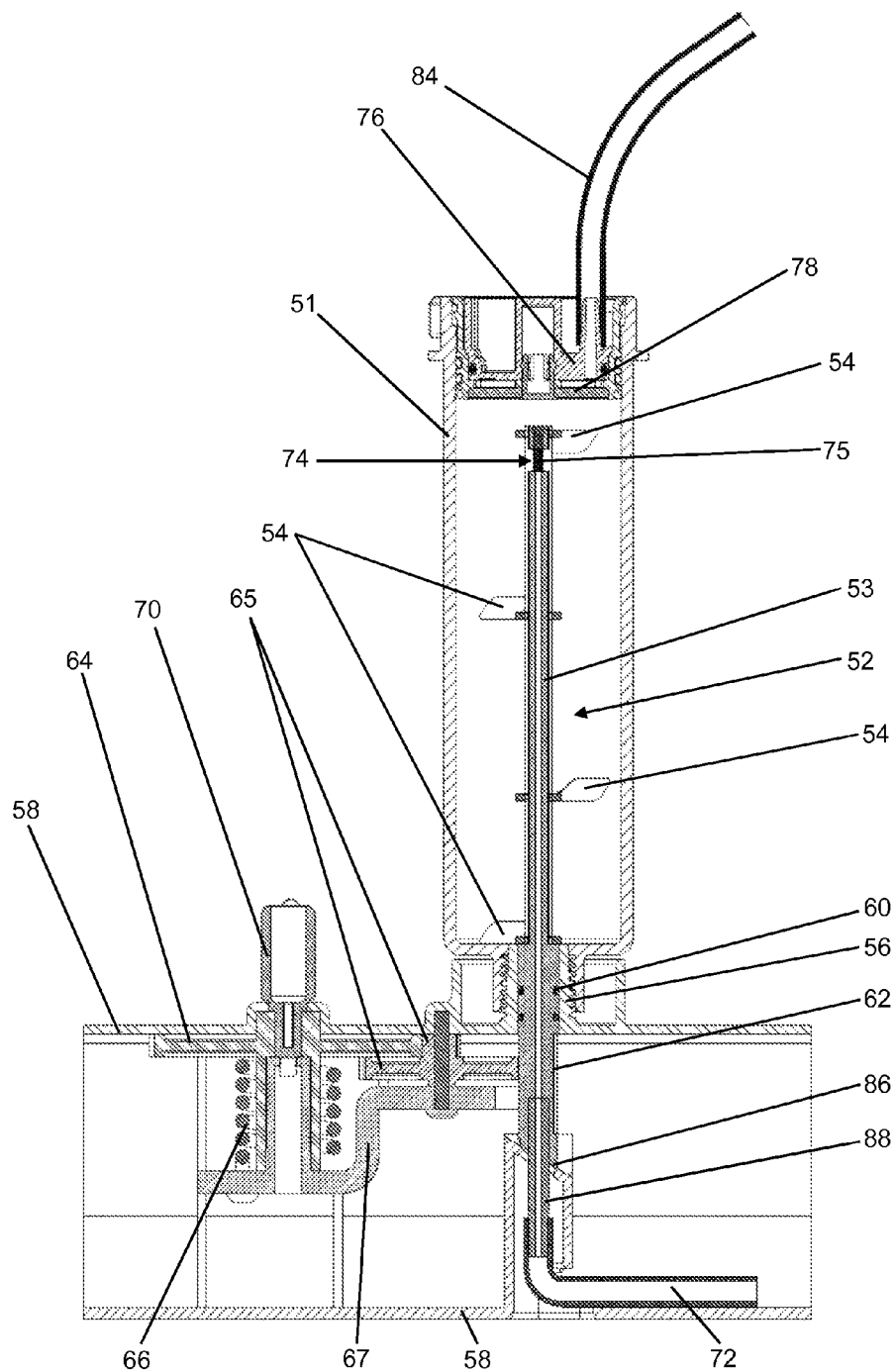

Further exemplary embodiments of the invention shall be illustrated in the following on the basis of five schematic figures, though without limiting the scope of the invention. In the figures:

FIG. 1: shows a schematic cross-sectional view of a detail of a vacuum mixing system according to the invention having a mixing device according to the invention for implementation of a method according to the invention;

FIG. 2: shows a schematic cross-sectional view of the design according to FIG. 1 in unlocked condition and with the drive running;

FIG. 3: shows a perspective schematic partial-sectional view of the design according to FIG. 1;

FIG. 4: shows a perspective schematic partial-sectional view of a detail of an alternative vacuum mixing system according to the invention having a mixing device according to the invention for implementation of a method according to the invention; and FIG. 5: shows a schematic cross-sectional view of the design according to FIG. 4.

FIGS. 1 and 2 shows a schematic cross-sectional views of a detail of a vacuum mixing system according to the invention having a mixing device according to the invention for implementation of a method according to the invention, and FIG. 3 shows a perspective schematic partial-sectional view thereof. FIGS. 1 and 3 show a locked condition and FIG. 2 shows an unlocked condition.

The vacuum mixing system has a cement cartridge 1 that consists of a plastic material and forms the boundary of a cylindrical mixing space 2 on its inside. A floor-side dispensing opening (on the bottom in FIGS. 1 and 2) has a stirrer shaft 3 guided through it, which is supported such that it can rotate and has four mixing vanes 4 attached to it as mixing elements. The mixing vanes 4 are connected by means of joints to the stirrer shaft 3 and can thus be placed against the stirrer shaft 3 in order to be able to insert and pull out the stirrer shaft 3 through the floor-side dispensing opening into and from the mixing space 2. Alternatively, it is feasible just as well to attach groups of mixing vanes 4 as mixing elements on the stirrer shaft 3.

The dispensing opening comprises an internal thread and the cement cartridge 1 is screwed onto an external thread of a socket 6 by means of said internal thread. The subject 6 is part of a base 8 on which the entire vacuum mixing system is built up. The stirrer shaft 3 seals the dispensing opening. For this purpose, two sealing rings 10 made of rubber are arranged on the external circumference of the stirrer shaft 3. The stirrer shaft 3 is widened in this region to enable the insertion and retraction of the stirrer shaft 3 while the mixing vanes 4 are placed against it. Accordingly, the stirrer shaft 3 has a smaller external diameter in the region of the mixing vanes 4.

A cogwheel 12 is formed in the stirrer shaft 3, below the seals 10 (on the bottom in FIGS. 1 and 2), by means of which the stirrer shaft 3 can be rotated about its own rotation axis and/or by means of which a rotary motion of the stirrer shaft 3 about its own axis can be driven. During this kind of rotation, the mixing vanes 4 also rotate in the mixing space 2 and thus provide for the mixing of a PMMA bone cement (not shown) and/or of its starting components (not shown) that is/are present in the mixing space 2. Due to the centrifugal forces thus arising, the mixing vanes 4 might lift off the stirrer shaft 3. Wipers (not shown) are provided on the mixing vanes 4 and touch against the internal wall of the cement cartridge 1 and/or against the boundaries of the mixing space 2 in operation, i.e. during the rotation, such that the mixing ware in the mixing space 2 can be mixed completely.

A cogwheel 14 of a gear engages the cogwheel 12 of the stirrer shaft 3. The cogwheel 14 comprises an internal separation and has at least twice as many cogs as the cogwheel 12. This attains a transmission such that a ¾ rotation of the cogwheel 14 causes the cogwheel 12, and thus the stirrer shaft 3, to perform more than one full rotation about its own axis.

To drive the motion of the cogwheel 14 of the gear, a tensioned coil spring 16 made of metal is attached to the cogwheel 14. The gear and the spring 16 are arranged inside the base 8, which forms a housing made of plastic for this purpose. In the locked condition (FIGS. 1 and 3), the gear and/or the cogwheel 14 are secured through a lock 18 in the form of a pin having a handle. For this purpose, the lock 18 is guided through an opening in the base 8 and is plugged into a recess on the outer circumference of the cogwheel 14 such that the cogwheel 14 is blocked from performing a motion and thus the tensioned spring 16 cannot relax. In unlocked condition (FIG. 2), the lock 18 simply has been pulled out. The coil spring 16 relaxes and thus drives the cogwheel 14 and thus the stirrer shaft 3. The elastic energy stored in the tensioned coil spring 16 can thus be used to mix the content of the mixing space 2 by means of the mixing elements 4. Accordingly, the coil spring 16 is an elastically deformable energy-storing element 16, in which elastic energy can be stored as a short-time drive for the mixing process.

The coil spring 16 can be wound up much like a watch using a wind-up wing pin 20. In this context, the wings of the wind-up wing pin 20 simplify the handling. The wind-up wing pin 20 ends in a hexagon or any other shape differing from cylindrical geometry. For this purpose, the hexagon can be plugged into a hexagonal hole 40 (shown in FIG. 2 only) that is firmly connected, axially, to the coil spring 16. However, it is feasible just as well to deliver the vacuum mixing system and/or the mixing device in pre-tensioned condition without the wind-up wing pin 20.

A conduit to 22 is arranged in the base 8 and is connected, through-going, to a conduit in the stirrer shaft 3. The conduit 22 does not end as shown in FIGS. 1 to 3, but continues (towards the left in FIGS. 1 to 3) and is connected to a monomer liquid container (not shown) in this location. Accordingly, the stirrer shaft 3 is provided in the form of a tube. The tube of stirrer shaft 3 ends via openings 24 and a porous core 25 into the mixing space 2. The porous core 25 is impermeable for powder, but permeable for liquids. This allows to ensure that a cement powder (not shown), as first starting component for the PMMA bone cement, that is present in the mixing space 2 cannot penetrate into the tube of the stirrer shaft 3, whereas the monomer liquid (not shown), as second starting component for the PMMA bone cement, can be guided from the monomer liquid container through the porous core 25 and the openings 24 via the tube of the stirrer shaft 3 and the conduit 22 into the mixing space 2.

A two-part dispensing plunger consisting of a sealing plunger 26 and a sterilisation plunger 28 is arranged on the side of the cement cartridge 1 opposite from the dispensing opening (on the top in FIGS. 1 and 2). The dispensing plunger is arranged in the mixing space 2 such as to be axially mobile and is locked on the upper end in detachable manner. The content of the mixing space 2 can be squeezed through the dispensing opening by means of the dispensing plunger, when the stirrer shaft 3 is taken out. The sterilisation plunger 28 is sealed with respect to the internal wall of the cement cartridge 1 by means of two circumferential seals 30. The sterilisation plunger 28 comprises a pore disk by means of which a powder cannot exit from the mixing space 2 to get outside, whereas a sterilising gas, such as, for example, ethylene oxide can be fed in. After the mixing space 2 and the cement powder in it was sterilised with the ethylene oxide, the sealing plunger 26 is inserted into the sterilisation plunger 28. The sealing plunger 26 comprises a circumferential seal 32 that seals the sealing plunger 26 with respect to the sterilisation plunger 28. Inserted into each other, the sealing plunger 26 and the sterilisation plunger 28 then form the two-part dispensing plunger.

The sealing plunger 26 has a bushing with a connector socket for the vacuum hose 34 arranged in it. The mixing space 2 can be evacuated through the vacuum hose 34 and the bushing of the sealing plunger 26. As a result, the monomer liquid can also be aspirated through the conduit 22 into the mixing space 2 and the two starting components can be mixed in a vacuum in the mixing space 2. For this purpose, the vacuum hose 34 is connected to an external or internal (belonging to the vacuum mixing system) vacuum source.

The stirrer shaft 3 ends in a cam disc 36 outside of the mixing space 2 (on the bottom in FIGS. 1 to 3). The cam disc 36 is formed by a bevelling of the end of the stirrer shaft 3. The cam disc 36 situated on a similarly bevelled and affixed socket of the base 8. Upon a rotation of the stirrer shaft 3, the cam disc 36 is pushed upwards and then lowered again during a full rotation. As a result, the stirrer shaft 3 and the mixing elements 4 are periodically moved up and down in the mixing space 2 during a rotation of the stirrer shaft 3. This attains additional mixing of the content of the mixing space 2. To ensure that the tube of the stirrer shaft 3 does not detach from the conduit 22 during this motion, a connector part 38, in the form of a tube that can be shifted in longitudinal direction, is provided and can be shifted in a connection of the conduit 22.

The PMMA bone cement can be produced and, if applicable, applied as follows using the set-up shown in the FIGS. 1 to 3:

The spring 16 is tensioned and locked by the lock 18 or the spring 16 is being tensioned by means of the wind-up wing pin 20 and is subsequently being locked. The monomer liquid container is opened. The mixing space 2 containing the cement powder is evacuated via the vacuum hose 34 and the monomer liquid is aspirated into the mixing space 2 through the conduit 22, the connector part 38, the tube of the stirrer shaft 3, the porous core 25, and the openings 24.

The lock is pulled out and/or removed. The spring 16 drives the cogwheel 14 and the cogwheel 14 drives the cogwheel 12. As a result, the stirrer shaft 3 is being rotated and moves during the rotation because the cam disk 36 slides up and down on the bevelled socket in the housing of the base 8. This is associated with the mixing vanes 4 also being rotated, lifted, and lowered in the mixing space 2, which causes the starting components to be mixed in the mixing space 2.

After the mixing is complete, the cement cartridge 1 containing the mixed cement dough is unscrewed from the base 8 and the stirrer shaft 3 with the mixing vanes 4 attached to it is pulled out of the dispensing opening. A dispensing tube (not shown) that can, but does not have to, contain an additional static mixer is screwed into the dispensing opening. The locking of the dispensing plunger to the internal wall of the cement cartridge 1 is released and the dispensing plunger is driven forward in the direction of the dispensing opening. As a result, the content of the mixing space 2 is propelled through the dispensing opening and the mixed PMMA bone cement can thus be applied.

FIGS. 4 and 5 show a perspective schematic partial-sectional view and a schematic cross-sectional view of a detail of an alternative vacuum mixing system according to the invention having a mixing device according to the invention for implementation of a method according to the invention.

The vacuum mixing system has a cement cartridge 51 that consists of a plastic material and forms the boundary of a cylindrical mixing space 52 on its inside. A floor-side dispensing opening (on the bottom in FIG. 5) has a stirrer shaft 53 guided through it, which is supported such that it can rotate and has four mixing vanes 54 attached to it as mixing elements. The mixing vanes 54 are connected by means of joints to the stirrer shaft 53 and can thus be placed against the stirrer shaft 53 in order to be able to insert and pull out the stirrer shaft 53 through the floor-side dispensing opening into and from the mixing space 52. Alternatively, it is feasible just as well to attach groups of mixing vanes 54 as mixing elements on the stirrer shaft 53.

The dispensing opening comprises an internal thread and the cement cartridge 51 is screwed onto an external thread of a socket 56 by means of said internal thread. The subject 56 is part of a base 58 on which the entire vacuum mixing system is built up. The stirrer shaft 53 seals the dispensing opening. For this purpose, two sealing rings 60 made of rubber are arranged on the external circumference of the stirrer shaft 53. The stirrer shaft 53 is widened in this region to enable the insertion and retraction of the stirrer shaft 53 while the mixing vanes 54 are placed against it. Accordingly, the stirrer shaft 53 has a smaller external diameter in the region of the mixing vanes 54.

A cogwheel 62 is formed in the stirrer shaft 53, below the seals 60 (on the bottom in FIGS. 4 and 5), by means of which the stirrer shaft 53 can be rotated about its own rotation axis and/or by means of which a rotary motion of the stirrer shaft 53 about its own axis can be driven. During this kind of rotation, the mixing vanes 54 also rotate in the mixing space 52 and thus provide for the mixing of a PMMA bone cement (not shown) and/or of its starting components (not shown) that is/are present in the mixing space 52. Due to the centrifugal forces thus arising, the mixing vanes 54 might lift off the stirrer shaft 53. Wipers (not shown) are provided on the mixing vanes 54 and touch against the internal wall of the cement cartridge 51 and/or against the boundaries of the mixing space 52 in operation, i.e. during the rotation, such that the mixing ware in the mixing space 52 can be mixed completely.

The cogwheel 62 of the stirrer shaft 53 is driven by a cogwheel 64 by means of two further cogwheels 65, which are jointly arranged on an axle. The cog wheels 64, 65 form a gear with multiple transmission that is used to drive the stirrer shaft 53. Unlike the embodiment according to FIGS. 1 to 3, the cogwheel 64 comprises a serration on the outside. Moreover, the gear according to the present embodiment comprises an additional gear unit stage, i.e. the cogwheels 65. This attains a high transmission ratio of the gear of at least eight to one (8:1) such that a full rotation of the cogwheel 64 causes the cogwheel 62, and thus the stirrer shaft 53, to perform at least eight full rotation about its own axis.

To drive the motion of the cogwheels 64, 65 of the gear, a tensioned coil spring 66 made of metal or plastics is attached to the cogwheel 64. The gear and the spring 66 are arranged inside the base 58, which forms a housing made of plastic for this purpose. In locked condition, the gear and/or the cog wheels 64, 65 are secured by means of a lock (not shown) in the form of a pin having a handle. For this purpose, the lock is guided through an opening in the base 58 and is plugged into a recess 69 in the cogwheel 64 such that the cogwheel 64 is blocked from performing a motion and thus the tensioned spring 66 cannot relax. In unlocked condition, the lock simply has been pulled out. The coil spring 66 relaxes and thus drives the cogwheel 64 and, by means of it, the cog wheels 65 and thus the stirrer shaft 63. The elastic energy stored in the tensioned coil spring 66 can thus be used to mix the content of the mixing space 52 by means of the mixing elements 54. Accordingly, the coil spring 66 is an elastically deformable energy-storing element 66, in which elastic energy can be stored as a short-time drive for the mixing process.

The coil spring 66 can be wound up much like a watch using a wind-up wing pin 70. In this context, the wings of the wind-up wing pin 70 simplify the handling. The wind-up wing pin 70 ends in a flat plate or any other shape differing from cylindrical geometry. For this purpose, the it can be plugged into a matching hole 40 not shown) that is firmly connected, axially, to the coil spring 66. However, it is feasible just as well to deliver the vacuum mixing system and/or the mixing device in pre-tensioned condition without the wind-up wing pin 70.

A conduit to 72 is arranged in the base 58 and is connected, through-going, to a conduit in the stirrer shaft 53. The conduit 72 does not end as shown in FIGS. 4 and 5, but continues (towards the right in FIGS. 4 and 5) and is connected to a monomer liquid container (not shown) in this location. Accordingly, the stirrer shaft 53 is provided in the form of a tube. The tube of the stirrer shaft 53 ends via openings 74 and a porous core 25 into the mixing space 52. The porous core 75 is impermeable for powder, but permeable for liquids. This allows to ensure that a cement powder (not shown), as first starting component for the PMMA bone cement, that is present in the mixing space 52 cannot penetrate into the tube of the stirrer shaft 53, whereas the monomer liquid (not shown), as second starting component for the PMMA bone cement, can be guided from the monomer liquid container through the porous core 75 and the openings 74 via the tube of the stirrer shaft 53 and the conduit 72 into the mixing space 52.

A two-part dispensing plunger consisting of a sealing plunger 76 and a sterilisation plunger 78 is arranged on the side of the cement cartridge 51 opposite from the dispensing opening (on the top in FIGS. 4 and 5). The dispensing plunger is arranged in the mixing space 52 such as to be axially mobile and is locked on the upper end in detachable manner. The content of the mixing space 52 can be squeezed through the dispensing opening by means of the dispensing plunger, when the stirrer shaft 53 is taken out. The sterilisation plunger 78 is sealed with respect to the internal wall of the cement cartridge 51 by means of two circumferential seals. The sterilisation plunger 78 comprises a pore disk by means of which a powder cannot exit from the mixing space 52 to get outside, whereas a sterilising gas, such as, for example, ethylene oxide can be fed in. After the mixing space 52 and the cement powder in it was sterilised with the ethylene oxide, the sealing plunger 76 is inserted into the sterilisation plunger 78. The sealing plunger 76 comprises a circumferential seal that seals the sealing plunger 76 with respect to the sterilisation plunger 78. Inserted into each other, the sealing plunger 76 and the sterilisation plunger 78 then form the two-part dispensing plunger.

The sealing plunger 76 has a bushing with a connector socket for the vacuum hose 84 arranged in it. The mixing space 52 can be evacuated through the vacuum hose 84 and the bushing of the sealing plunger 76. As a result, the monomer liquid can also be aspirated through the conduit 72 into the mixing space 52 and the two starting components can be mixed in a vacuum in the mixing space 52. For this purpose, the vacuum hose 84 is connected to an external or internal (belonging to the vacuum mixing system) vacuum source.

The stirrer shaft 53 ends in a cam disc 86 outside of the mixing space 52 (on the bottom in FIGS. 4 and 5). The cam disc 86 is formed by a bevelling of the end of the stirrer shaft 53. The cam disc 86 situated on a similarly bevelled and affixed socket of the base 58. Upon a rotation of the stirrer shaft 53, the cam disc 86 is pushed upwards and then lowered again during a full rotation. As a result, the stirrer shaft 53 and the mixing elements 54 are periodically moved up and down in the mixing space 52 during a rotation of the stirrer shaft 3. This attains additional mixing of the content of the mixing space 52. To ensure that the tube of the stirrer shaft 53 does not detach from the conduit 72 during this motion, a connector part 88, in the form of a tube that can be shifted in longitudinal direction, is provided and can be shifted in a connection of the conduit 72.

The PMMA bone cement can be produced and, if applicable, applied as follows using the set-up shown in the FIGS. 4 and 5:

The spring 66 is tensioned and locked by the lock or the spring 66 is being tensioned by means of the wind-up wing pin 70 and is subsequently being locked. The monomer liquid container is opened. The mixing space 52 containing the cement powder is evacuated via the vacuum hose 84 and the monomer liquid is aspirated into the mixing space 52 through the conduit 72, the connector part 88, the tube of the stirrer shaft 53, the porous core 75, and the openings 74.

The lock is pulled out and/or removed. The spring 66 drives the cogwheel 64, the cogwheel 64 drives the smaller cogwheel 65 (on the top in FIGS. 4 and 5), and the larger cogwheel 65 (on the bottom in FIGS. 4 and 5) drives the cogwheel 62 on the stirrer shaft 53. As a result, the stirrer shaft 53 is being rotated and moves during the rotation because the cam disk 86 slides up and down on the bevelled socket in the housing of the base 58. This is associated with the mixing vanes 54 also being rotated, lifted, and lowered in the mixing space 52, which causes the starting components to be mixed in the mixing space 52.

After the mixing is complete, the cement cartridge 51 containing the mixed cement dough is unscrewed from the base 58 and the stirrer shaft 53 with the mixing vanes 54 attached to it is pulled out of the dispensing opening. A dispensing tube (not shown) that can, but does not have to, contain an additional static mixer is screwed into the dispensing opening. The locking of the dispensing plunger to the internal wall of the cement cartridge 51 is released and the dispensing plunger is driven forward in the direction of the dispensing opening. As a result, the content of the mixing space 52 is propelled through the dispensing opening and the mixed PMMA bone cement can thus be applied.

The features of the invention disclosed in the preceding description and in the claims, figures, and exemplary embodiments, can be essential for the implementation of the various embodiments of the invention both alone and in any combination.

LIST OF REFERENCE NUMBERS 1, 51 Cement cartridge
2, 52 Mixing space
3, 53 stirrer shaft
4, 54 Mixing vanes/mixing element
6, 56 Socket
8, 58 Base
10, 60 Seal
12, 62 Cogwheel of the stirrer shaft
14, 64 Cogwheel of the gear
16, 66 Spring/coil spring
18 Lock
20, 70 Wind-up wing pin
22, 72 Conduit
24, 74 Opening
25, 75 Porous core
26, 76 Sealing plunger
28, 78 Sterilisation plunger
30 Seal
32 Seal
34, 84 Vacuum hose
36, 86 Cam disc
38, 88 Connector part
40 Hexagonal hole
65 Cogwheel of the gear
67 Bracketing
69 Recess

The invention claimed is:

1. A mixing device for mixing bone cement, the mixing device comprising:
   a mixing space for the mixing of the bone cement;
   at least one mixing element that is supported in the mixing space such that it is rotatable;
   a gear for driving the rotation of the at least one mixing element;
   at least one elastically deformable energy-storing element connected to the gear such that the gear can be driven by an elastic energy from the energy- storing element and such that the at least one mixing element is rotatable in the mixing space by means of the gear upon the release of elastic energy from the energy-storing element; and
   a cam disc, slidable up and down, connected to the at least one mixing element, wherein motion of the cam disc influences the at least one mixing element such that the at least one mixing element performs at least one periodical axial stroke motion during rotary motion of the at least one mixing element.

2. The mixing device according to claim 1, wherein the at least one mixing element is arranged on a stirrer shaft, supported such that it can rotate, and in that a rotation of the stirrer shaft is drivable by the gear, whereby the stirrer shaft is guided out of the mixing space through a gas-tight or pressure-tight bushing and is connected to the gear outside of the mixing space.

3. The mixing device according to claim 2, wherein the stirrer shaft is hollow and forms a conduit for a liquid starting component of the bone cement.

4. The mixing device according to claim 1, wherein the at least one mixing element is a plurality of mixing vanes, wherein the mixing vanes extend into the mixing space such as to be radial to the rotation axis during the rotation of the mixing vanes in the mixing space and are inclined with respect to a plane perpendicular to the rotation axis.

5. The mixing device according to claim 4, wherein the mixing vanes are attached or attachable to a stirrer shaft, wherein the mixing vanes are arranged on the stirrer shaft at an axial offset from each other.

6. The mixing device according to claim 5, wherein the mixing vanes are attached to the stirrer shaft by means of a joint, such that the mixing vanes can be placed against the stirrer shaft.

7. The mixing device according to claim 5, wherein the mixing vanes are attached to the stirrer shaft in detachable manner, such that the mixing vanes are separatable from the stirrer shaft while the stirrer shaft is being pulled out of the mixing space.

8. The mixing device according to claim 1, wherein the gear and/or the elastically deformable energy-storing element are locked by means of at least one detachable mechanical lock such that a release of the energy from the energy-storing element is prevented, wherein the at least one mechanical lock is a safety catch and/or a safety pin.

9. The mixing device according to claim 1, wherein the gear is a cogwheel gear, a friction wheel gear or a power transmission gear.

10. The mixing device according to claim 1, wherein the elastically deformable energy-storing element is a spring element that is connectable to the gear, wherein the gear can be driven by the spring force of the tensioned spring element, wherein the spring element is a metal spring, a steel leg spring, a steel leaf spring or a steel coil spring.

11. The mixing device according to claim 1, wherein a release of elastic energy from the energy-storing element effects a rotary motion of the gear, that the gear effects a transmission ratio of at least 2:1 with respect to the at least one.

12. A vacuum mixing system comprising:
   the mixing device according to claim 1, wherein the mixing space contains a cement powder;
   a monomer container filled with a fluid monomer; and
   a conduit connecting the monomer container to the mixing space in a liquid-permeable manner.

13. The vacuum mixing system according to claim 12, further comprising:
   A base at which a cartridge containing the mixing space is attached in detachable manner and at which the monomer container is attached, wherein the conduit and the elastic energy-storing element are arranged in or on the base.

14. The vacuum mixing system according to claim 12, wherein a drive axle extends through a seal out of the mixing space and a cogwheel or friction wheel is attached on the part of the drive axle that is arranged outside of the mixing space and is connected to the gear, wherein the drive axle is drivable by means of the cogwheel or friction wheel.

15. The vacuum mixing system according to claim 14, wherein the mixing space is a part of a cement cartridge, wherein the cement cartridge is dosed on one side by a dispensing plunger or a dispensing plunger system, wherein the dispensing plunger or the dispensing plunger system is axially mobile in the mixing space and is configured for expelling ready-mixed bone cement, and in that the closure thus formed is impermeable for the cement powder and is permeable for a gas, wherein the cement cartridge, before the cement components are being mixed, can be closed appropriately in vacuum-tight manner such that a transfer of the monomer liquid into the mixing space of the cement cartridge to the cement powder under the effect of a vacuum is made feasible.

16. The vacuum mixing system according to claim 15, wherein a device for generating a vacuum is integrated into the vacuum mixing system.

* * * * *